United States Patent [19]

Webster

[11] Patent Number: 4,601,881

[45] Date of Patent: Jul. 22, 1986

[54] LIQUID HANDLING SYSTEM

[75] Inventor: Milo E. Webster, Braintree, Mass.

[73] Assignee: Allied Corporation, Morristown, N.J.

[21] Appl. No.: 667,299

[22] Filed: Nov. 1, 1984

[51] Int. Cl.⁴ .................... G01N 21/00; G01N 31/00; G01N 33/00

[52] U.S. Cl. ........................................ 422/67; 422/68

[58] Field of Search ............... 137/559, 597, 861, 884, 137/608, 624.18; 251/61.1, 331; 422/63–67, 99, 68, 73, 79, 81, 82; 436/179, 180

[56] References Cited

U.S. PATENT DOCUMENTS

| | | | |
|---|---|---|---|
| 3,609,040 | 9/1971 | Kuzel | 356/36 |
| 3,613,729 | 10/1971 | Dora | 137/624.18 |
| 3,900,289 | 8/1975 | Liston | 23/230 |
| 3,934,611 | 1/1976 | Gachot et al. | 137/608 |
| 3,951,167 | 4/1976 | Howell et al. | 137/608 |
| 3,963,440 | 6/1976 | Stein et al. | 23/253 |
| 4,108,602 | 8/1978 | Hanson et al. | 23/230 |
| 4,168,294 | 9/1979 | Calzi et al. | 422/68 |
| 4,219,530 | 8/1980 | Kopp et al. | 422/69 |
| 4,304,257 | 12/1981 | Webster | 137/559 |

Primary Examiner—Frank Sever
Attorney, Agent, or Firm—Lowell H. McCarter

[57] ABSTRACT

A liquid handling system useful in apparatus for analyzing biological liquid specimens or the like includes a plurality of sample metering chambers, a distribution manifold connected between a sample inlet port and the sample metering chambers, and a corresponding plurality of auxiliary liquid metering chambers connected to corresponding auxiliary liquid reservoirs. Liquids are flowed from the sample inlet port through the distribution manifold to the sample metering chambers and from auxiliary liquid reservoirs to the auxiliary liquid metering chambers under the influence of reduced pressures which are selectively connected to the flow network through an integrated valve array and reduced pressure manifolds.

36 Claims, 7 Drawing Figures

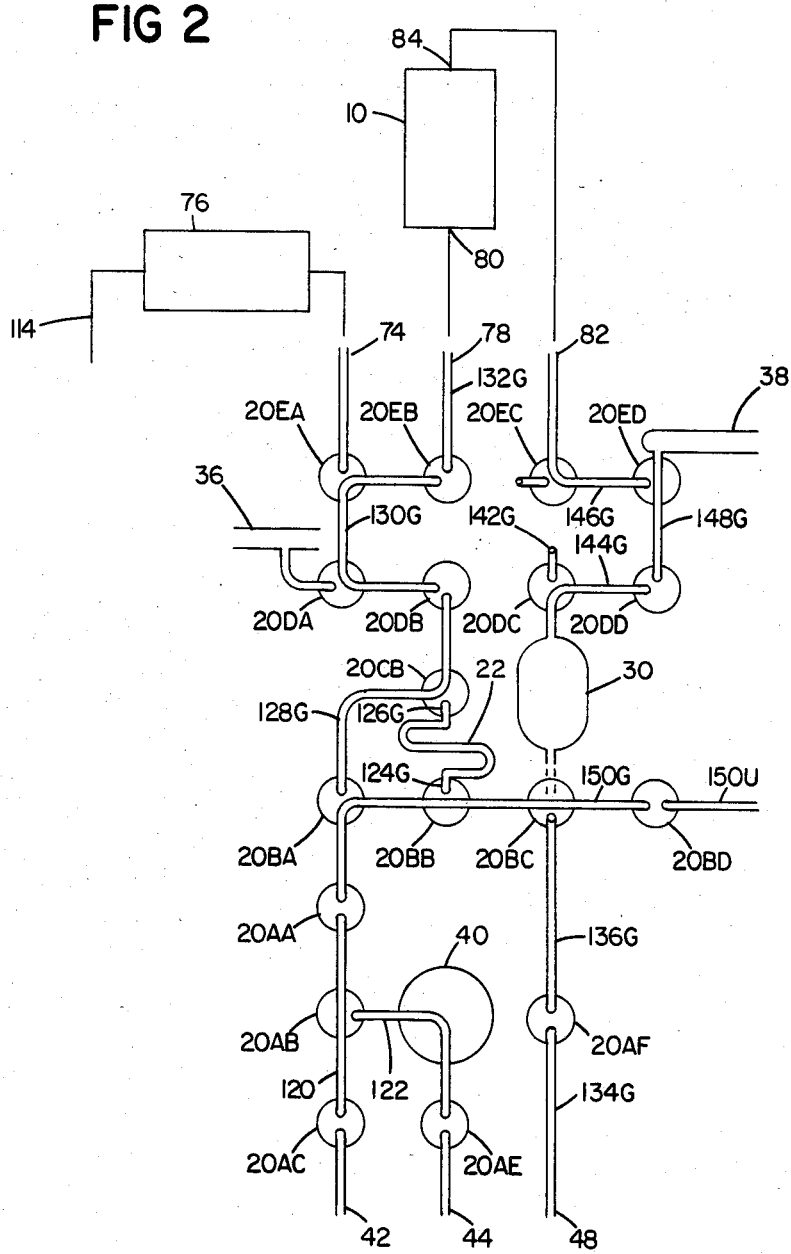

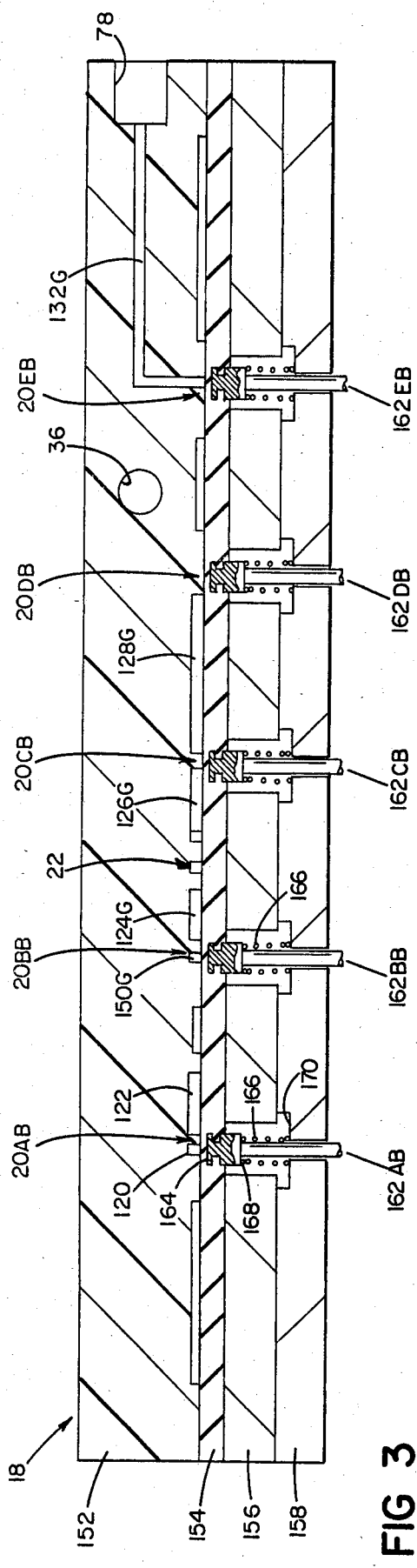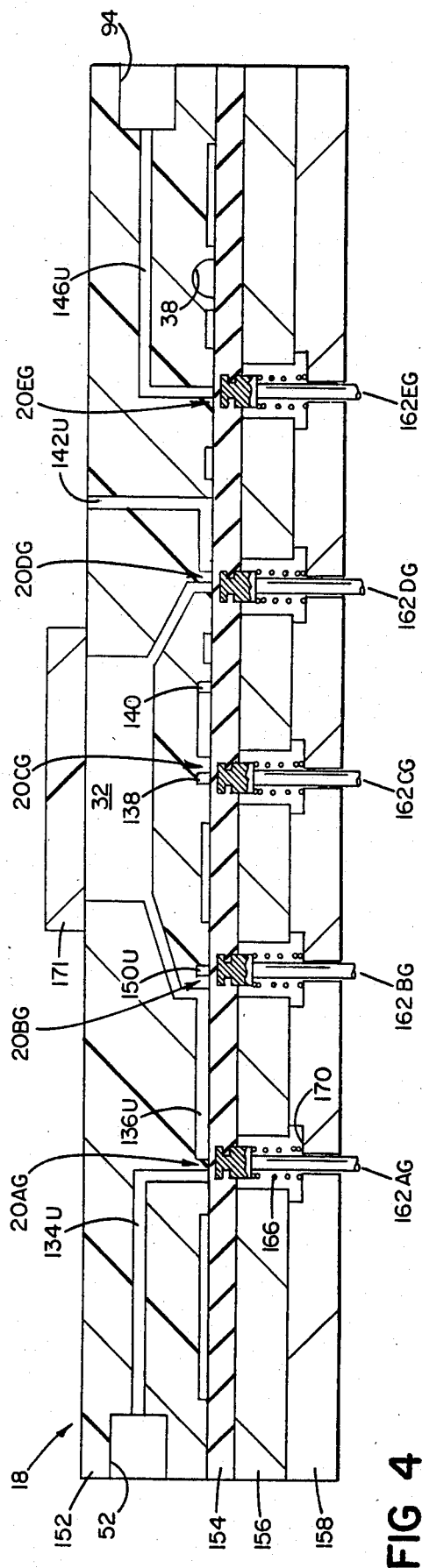

FIG 5
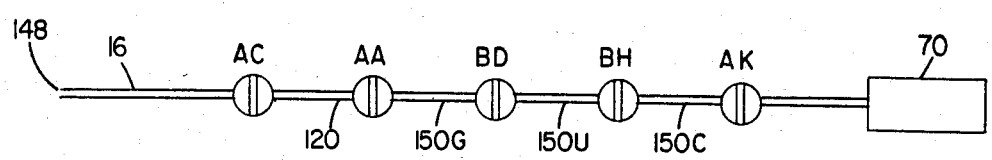
5a
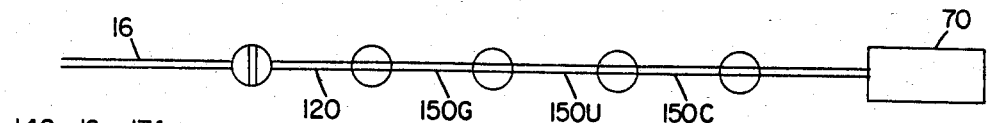
5b
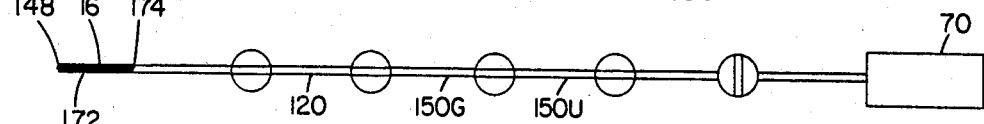
5c
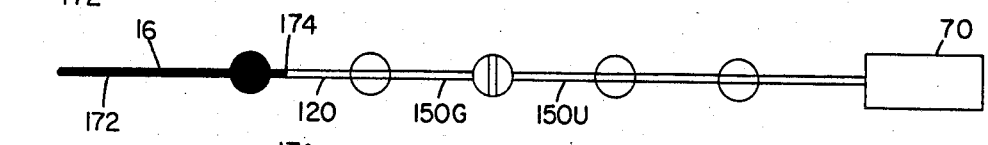
5d
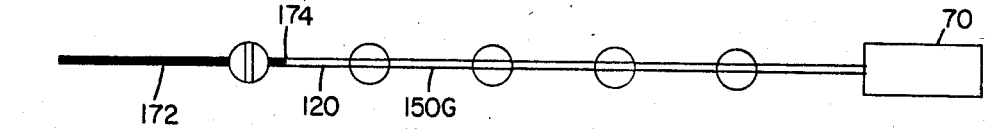
5e
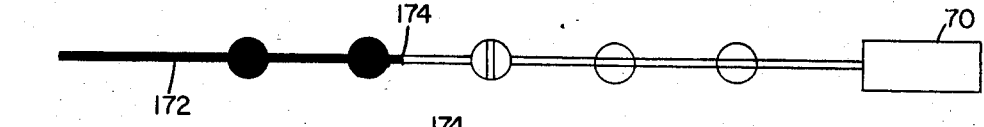
5f
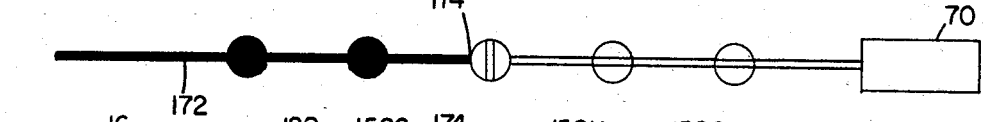
5g
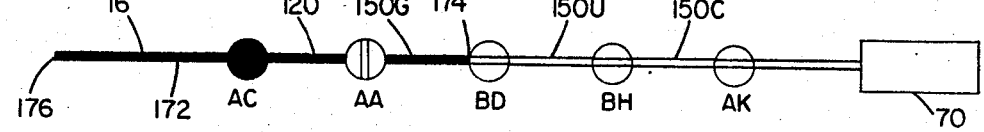
5h
FIG 6
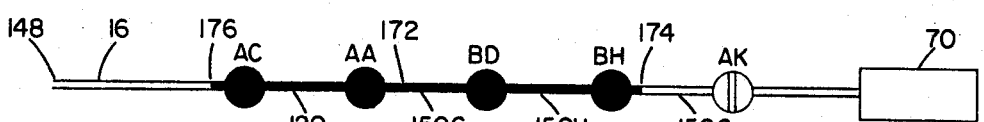
6a
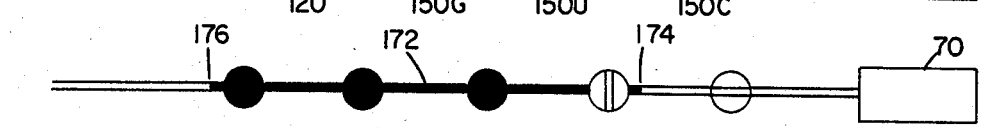
6b
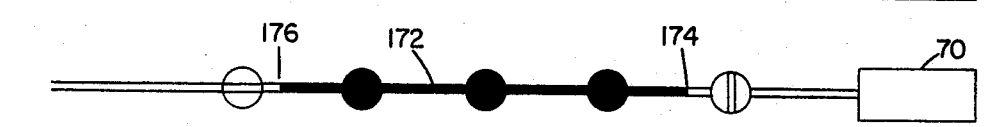
6c
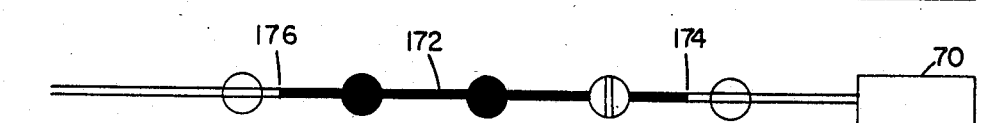
6d
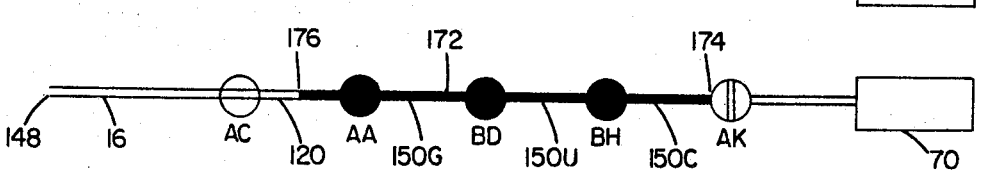
6e

LIQUID HANDLING SYSTEM

This invention relates to liquid handling systems and has particular application to apparatus for the analysis of constituents of biological liquids and the like.

In the analysis of specific constituents such as glucose, urea or creatinine of biological liquid samples such as whole blood, serum, plasma, and urine, a mixture of precise amounts of the sample to be analyzed and a prechosen reagent corresponding to the specific constituent of interest is disposed in an analysis cell through which a monochromatic beam of light of predetermined wavelength is passed to develop an output signal, which by suitable processing provides qualitative and quantative indications of the presence of the particular constituent of interest in the sample.

In such analyses, it is desirable to process minute quantities of the samples, particularly where the sample is a precious liquid and analyses for several constituents are desired. Such analyses would be more economical as smaller volumes of reagents are required. Further, it is desirable to provide analysis systems that are capable of performing plural analyses concurrently.

In accordance with one aspect of the invention there is provided a liquid handling system useful in apparatus for analyzing biological liquid specimens or the like which includes a plurality of sample metering chambers, a distribution manifold connected between a sample inlet port and the sample metering chambers, and a corresponding plurality of auxiliary liquid metering chambers connected to corresponding auxiliary liquid reservoirs. Fluids are flowed from the sample inlet port through the distribution manifold to the sample metering chambers and from auxiliary liquid reservoirs to the auxiliary liquid metering chambers under the influence of reduced pressures (that term herein referring to pressures that are less than atmospheric) which are selectively connected to the flow network through an integrated valve array and reduced pressure manifolds.

In preferred embodiments, each analysis channel has a sample metering chamber with an inlet and an outlet and a bypass line and valve arrays at the inlet and outlet, and an associated auxiliary liquid metering chamber that may be selectively connected to a reservoir of auxiliary liquid such as a reagent and to the sample metering chamber. A valve control system applies reduced pressures to flow sample and auxiliary liquid into corresponding chambers to fill those chambers so that precisely measured quantities are available, and then the precisely measured quantities are flowed to analysis chambers where they are mixed, degassed and spectrophotometrically analyzed.

In a particular embodiment, valves and metering chambers are in a flow network array that includes a face plate member with a firm and stable support surface, and a flexible sheet member that is clamped in conforming and mating engagement to the firm and stable face plate surface. A flow channel network is formed in one of the engaged surfaces with each valve including a land portion that separates adjacent flow channel portions. Each valve also includes an actuator which is arranged to flex the sheet member between a first position in which the surface of the valve sheet member is in mating and sealing engagement with the surface of the face plate member so that the valve land portion blocks flow between the adjacent channel portions, and a second position in which the sheet surface is spaced from the first position and allows liquid flow across the land surface between the adjacent channel portion. Each valve has a small volume (less than ten microliters) when open, and essentially zero dead space when closed. The gentle and smooth closing action of the valve membrane is in a radially inward direction and the valves provide excellent isolation between different liquids which are handled by the system.

In a particular embodiment, the valve face plate member is transparent, and sample flow paths are in the form of grooves that extend along the face plate surface, while the flexible valve sheet is opaque and of contrasting color to the sample liquids to be analyzed. In that particular embodiment, there are four sample metering chambers, a $7\frac{1}{2}$ microliter volume chamber for glucose analysis, a $3\frac{1}{2}$ microliter sample chamber for urea analysis, and $3\frac{1}{2}$ microliter and 10 microliter sample measuring chambers for creatinine analysis, together with corresponding reagent metering chambers associated with each analysis channel. The flow network also includes a positive displacement pump mechanism for flowing flush liquid through the sample inlet line between analysis sequences. Other flow networks are coordinated with the valving array to provide effective cleaning of flow surfaces and chambers between analysis sequences.

Other features and advantages of the invention will be seen as the following description of a particular embodiment progresses, in conjunction with the drawings, in which:

FIG. 2 is a diagram of the glucose channel portion of the flow network structure employed in the apparatus shown in FIG. 1;

FIG. 3 is a sectional view in part through the sample measuring chamber of the glucose channel, taken along the line 3—3, of FIG. 1;

FIG. 4 is a sectional view in part through the reagent measuring chamber of the urea channel taken along the line 4—4 of FIG. 1;

FIGS. 5 and 6 are a series of diagrammatic views of the sample distribution manifold in the flow network.

DESCRIPTION OF PARTICULAR EMBODIMENT

Figure 1:
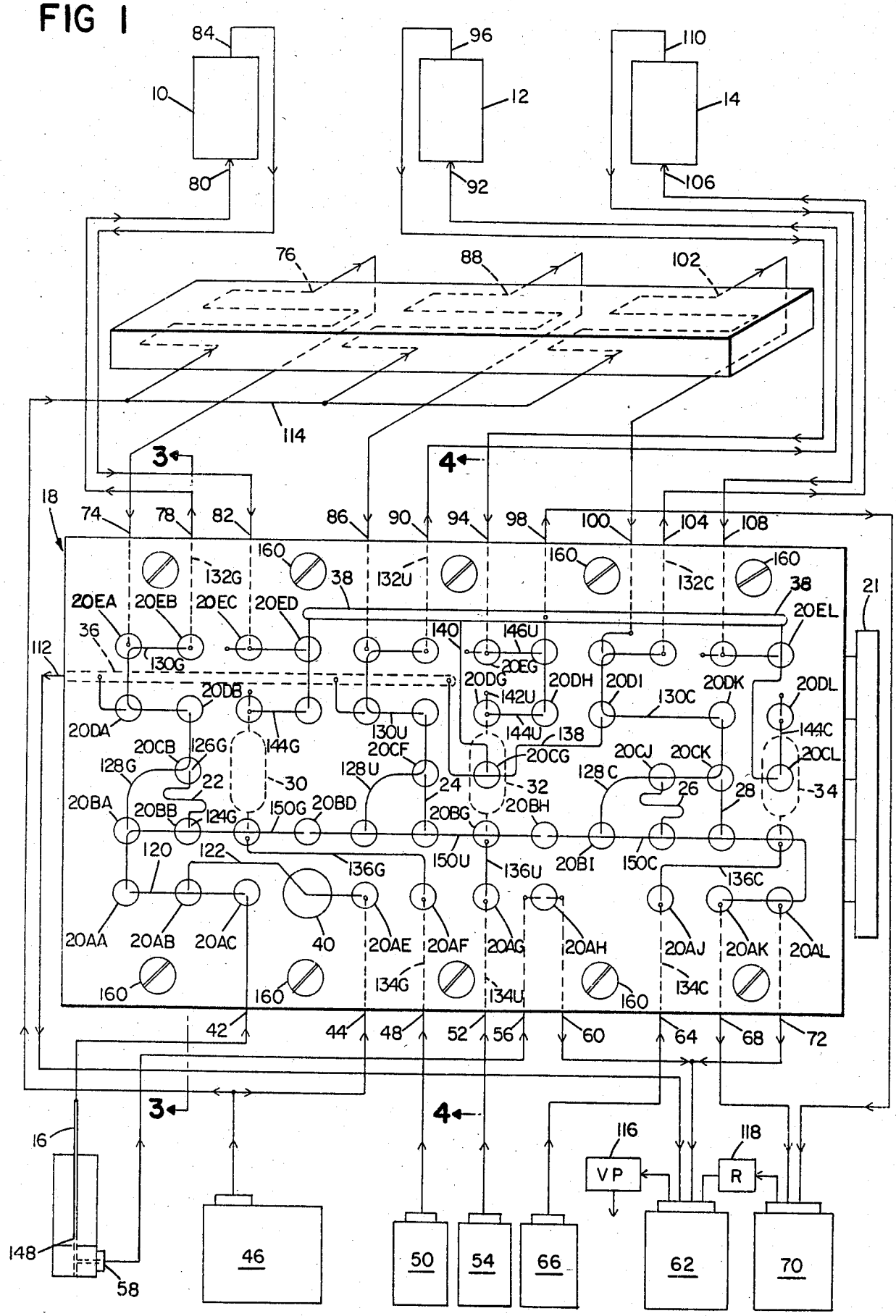
FIG. 1 is a front view of (partially in diagrammatic form) of a three channel analysis instrument in accordance with the invention.

Shown in FIG. 1 is a diagrammatic view of a three channel analysis instrument with photometric analysis cell 10 for glucose analysis, a similar photometric analysis cell 12 for urea analysis, and a third similar photometric analysis cell 14 for creatinine analysis, each cell 10, 12, 14 having associated radiation source and radiation sensor apparatus for photometric analysis. Analysis cells 10, 12 and 14 are connected to sample inlet probe 16 by flow network structure 18 that includes an array of valves 20 of the type shown in Webster U.S. Pat. No. 4,304,257, the disclosure of which is specifically incorporated herein by reference, and that are operated by valve controller 21. Flow network structure 18 also includes a 7.5 microliter volume sample measuring chamber 22 associated with the glucose channel; a 3.5 microliter volume sample measuring chamber 24 associated with the urea channel, sample measuring chambers 26, 28 (ten microliter and 3.5 microliter volume respectively) associated with the creatinine channel; glucose reagent measuring chamber 30 (300 microliter volume); urea reagent measuring chamber 32 (600 microliter volume); creatinine reagent measuring chamber 34 (300 microliter volume); vacuum manifolds 36, 38 and pump chamber structure 40.

Flow network assembly 18 has an inlet 42 from sample probe 16; inlet 44 connected to flush reservoir 46; inlet 48 connected to glucose reagent reservoir 50; inlet 52 connected to urea reagent reservoir 54; inlet 56 connected to tap 58 of sample probe 16; outlet 60 connected to vacuum chamber 62; inlet 64 connected to creatinine reagent reservoir 66; outlet 68 connected to vacuum chamber 70; outlet 72 connected to vacuum chamber 62; inlet 74 connected to the outlet of the flush preheater section 76 for the glucose channel; outlet 78 connected to the inlet 80 of glucose analysis cell 10; inlet 82 connected to the outlet 84 of glucose analysis cell 10; inlet 86 connected to the outlet of the flush preheater section 88 associated with the urea channel; outlet 90 connected to the inlet 92 of the urea analysis cell 12; inlet 94 connected to the outlet 96 of cell 12; outlet 98 connected to vacuum chamber 70; inlet 100 connected to the outlet of flush preheater section 102 associated with the creatinine channel; outlet 104 connected to the inlet 106 of creatinine analysis cell 14; inlet 108 connected to the outlet 110 of creatinine analysis cell 14; and outlet 112 that connects manifold 36 to vacuum chamber 62. Flush reservoir 46 is also connected to manifold 114 that has inlets to preheater sections 76, 80 and 102; vacuum pump 116 is connected to vacuum chamber 62 to establish a vacuum on the order of 22-24 inches of mercury in chamber 62; and the two chambers 70 and 62 are interconnected by regulator 118 so that a regulated vacuum of about fifteen inches of mercury is established in chamber 70.

The flow network assembly 18 includes a rectangular array of valves 20 with the valves spaced on centers of about 1.5 centimeters and arranged in five rows A-E and twelve columns A-L. Thus, the valve connected to sample inlet port 42 is identified as valve 20AC, the valve connected to inlet port 74 is identified as valve 20EA, and the valve connected to outlet port 78 is identified as valve 20EB. With reference to the valves located along section line 3—3, (FIG. 1), valve 20AB is of the "isolation" type and isolates through channel 120 (that extends between isolation valves 20AA and 20AC) from channel 122 that extends to pump chamber 40; valve 20BB is an isolation valve that isolates distribution manifold section 150G from the inlet 124G to glucose sample metering chamber 22; valve 20CB isolates the outlet 126G of sample metering chamber 22 from the chamber bypass channel 128G that extends from isolation valve 20BA to isolation valve 20DB; and valve 20EB isolates the channel 130G (that extends from isolation valve 20DB through valves 20DA and 20EA to isolation valve 20EB) from channel 132G (that extends to outlet port 78).

With reference to the valves located along section line 4—4, valve 20AG isolates channel 134U (connected to port 52) from channel 136U which is in direct communication with urea reagent metering chamber 32; valve 20BG isolates channel 136U from distribution manifold 150; valve 20CG isolates channel 138 (which extends from isolation valve 20DI to vacuum manifold 36) from channel 140 (which extends to vacuum manifold 38 and provides a bypass or short circuit network between vacuum manifolds 36 and 38 for use during cleaning and flushing); valve 20DG is of the "vent" type that isolates vent 142U from the channel 144 (which extends between urea reagent metering chamber 32 and isolation valve 20DH); and valve 20EG is another "vent" valve which vents the channel 146 that extends from isolation valve 20EH to inlet port 94.

Flow network 18 has three similar but distinct flow channel sections, one for glucose analysis, a second for urea analysis and a third for creatinine analysis. Each channel includes a sample metering chamber and a reagent metering chamber of volume proportioned to the volume of the sample metering chamber so that the desired dilution is obtained. The creatinine analysis section has two sample metering chambers 26 and 28 so that different dilution ratios may be employed as desired. For example, chamber 26 may be employed with a serum creatinine analysis while chamber 28 (a greater dilution ratio) may be employed with a urine creatinine analysis. The sample to be analyzed is flowed to the three analysis sections via distribution manifold 150—isolation valves 20BD and 20BH in distribution manifold 150 serving to separate channel sections 150G, 150U and 150C.

Sample probe 16 is connected via inlet port 42 and valves 20AC, 20AB and 20AA to sample distribution manifold 150 that has a cross-sectional area of about 0.3 square millimeter so that a length of about twenty-five centimeters is provided for a seventy microliter sample volume. The glucose section 150G of that distribution manifold extends through valves 20BA, 20BB and 20CC to isolation valve 20BD; the urea section 150U extends through valves 20BE, 20BF and 20BG to isolation valve 20BH, and the creatinine section 150C extends through valves 20BI, 20BJ and 20BK, 20BL and 20AL to vacuum isolation valve 20AK. The three sample-reagent measuring and mixing networks that are connected to distribution manifold 150 are of similar configuration, the measuring and mixing network for the glucose channel being shown in slightly larger scale in diagrammatic form in FIG. 2.

In an operating sequence, the tip 148 of sample probe 16 is inserted (by a drive motor—not shown) into a sample cup and with valve 20AC closed, distribution manifold 150 is connected to vacuum chamber 70 to reduce the pressure in that manifold channel. After one quarter second, valve 20BD is then closed to seal the reduced pressure in distribution manifold 150G and when isolation valve 20AC is opened the sealed reduced pressure draws sample into the inlet probe towards distribution manifold 150. That valve sequence of alternate opening and closing valves 20AC and 20BD is repeated so that the volume of trapped reduced pressure between the leading edge of the sample and valve 20BD is progressively reduced until the leading edge of the sample is at valve 20BD in a self-limiting process—a seventy microliter volume of sample having been drawn into probe 16 and channels 120 and 150G. Sample probe 16 is then withdrawn from the sample cup and the seventy microliter sample is positioned in the distribution manifold 150 by sequential and alternate opening and closing of valves 20AA, 20BD, 20BH and 20AK until the leading edge of the sample is at valve 20AK in the same self-limiting liquid movement process.

After sample positioning, the three metering chambers 22, 24 and 26 (or 28) are sequentially filled from manifold 150 while the corresponding reagent metering chambers 30, 32 and 34 are being concurrently filled from their respective reservoirs 50, 54 and 66. After those six metering chambers are filled, adjacent flow paths (including the distribution manifold 150) are flushed to remove excess material. Then the metered second sample quantity and the corresponding metered reagent for each analysis channel are flowed in a mixing and dilution sequence into the corresponding analysis cell 10, 12, 14 (each of which has a volume about twice the volume of the reagent-sample mixture to be analyzed). Air is drawn through the diluted sample mixture in each analysis chamber in a bubbling action that provide further mixing and then the diluted mixture in each analysis chamber is subjected to reduced pressure for degassing. After an equilibration interval of about ten seconds, the three diluted samples are concurrently spectrophotometrically analyzed during which interval the flow network is flushed. After analysis, the analysis cells 10, 12 and 14 are emptied and cleaned in preparation for the next analysis sequence.

Further details of the flow network assembly 18 may be seen with reference to the sectional views of FIGS. 3 and 4. That flow network array includes transparent face plate 152 of cast acrylic resin. Clamped against the bottom surface of face plate 152 is manifold diaphragm sheet 154 of white polyurethane that has a smooth, pit-free surface. Apertured backing plate 156 is seated against diaphragm sheet 154 by mounting plate 158, and the stack of face plate 152, diaphragm 154, backing plate 156 and mounting plate 158 are secured together by resilient fasteners 160 (FIG. 1). Secured to diaphragm member 154 is an array of actuators 162, the head 164 of each being embedded in the polyurethane membrane sheet 154. A spring 166 seated between surface 168 of actuator 162 and surface 170 of mounting plate 158, maintaining membrane 154 in seated or valve closed position; and movement of actuator 162 away from face plate 152 opens the valve.

The sectional view of FIG. 3 is through glucose sample measuring chamber 22 and manifold 36 while the sectional view of FIG. 4 is through urea reagent measuring chamber 32 and manifold 38 as well as portions of the associated valves and interconnecting flow networks. Each of the reagent metering chambers 30, 32, 34 is entirely bounded by acrylic plastic, a sheet 171 of plastic being solvent bonded to the upper surface of face plate 152 to define the outer wall of chamber 32, the other reagent measuring chambers 30 and 34 being similarly formed.

Further details of the sample introduction sequence may be seen with reference to FIG. 5 which shows in diagrammatic form an operating sequence of the valves connected between sample inlet 148 and vacuum chamber 70. In that operating sequence, valves AC, AA, BD, BH and AK are initially closed (FIG. 5a) and probe 16 is moved down by a stepping motor to insert its tip 148 into the sample cup. After a one second delay, isolation valves AK, BH, BD and AA are opened (FIG. 5b) to allow the regulated vacuum from chamber 70 to reduce the pressure in distribution manifold 150 and inlet channel 120. After a ¼ second delay, isolation valve AK is closed (sealing that reduced pressure in channel 120 and manifold 150) and after a 1/10 second delay isolation valve AC is opened (FIG. 5c) so that the reduced pressure trapped by closed isolation valve AK draws sample 172 into probe 16 and towards valve BD. Isolation valve AC is then closed and isolation valve AK is opened to recharge manifold 150 with reduced pressure. After a delay of 1/10 of a second isolation valve BD is closed and isolation valve AC is opened (FIG. 5d) so that the reduced pressure trapped by closed isolation valve BD draws sample 172 further into probe 16 and past valve AC toward valve BD. After 1/10 of a second isolation valve AC is closed (clamping leading edge 174 of sample 172—FIG. 5e) and isolation valve BD is again opened to charge channel 120 and section 150G of the distribution manifold between leading edge 174 and valve BD with reduced pressure (FIG. 5e). Isolation valve BD is then again closed and isolation valve AC opened after 1/10 of a second for about ¼ of a second (releasing sample 172—FIG. 5f) so that the reduced pressure trapped between leading edge 174 and valve BD draws in the sample 172 further along the manifold 150G. The sequence of valve operations indicated in FIG. 5d–f when repeated four times draws in the sample 172 into probe 16 and positions its leading edge 174 at, but not beyond, valve BD (FIG. 5g) so that a seventy microliter volume of sample is drawn in to valve BD in a self-limiting process. When the leading edge 174 of sample 152 is at valve BD, valve AA is closed, as indicated in FIG. 5h, to "clamp" the sample 172 so that valves BD, BH and AK upstream from leading edge 174 may be opened to reduce the pressure in manifold sections 150U and 150C without movement of sample 172.

Sample probe 16 is then withdrawn and the seventy microliter sample 172 held in the sample probe 16 and connecting lines is positioned in distribution manifold 150 adjacent the three metering chambers 22, 24 and 26 (28) by a sequential operation of valves as indicated in FIG. 6. Valve AK is closed and then valves AA and BD are opened (FIG. 6a) to release sample 172 and allow the trapped reduced pressure to draw the sample towards valve AK. After a ¼ second interval, valve BH is closed (clamping sample 172 adjacent leading edge 174) and valve AK is opened to charge section 150C of the distribution manifold 150 between leading edge 174 and valve AK with reduced pressure. After about a 0.1 second delay, valve AK is closed (trapping the reduced pressure) and valve BH is opened (releasing sample 172) for about ¼ second (FIG. 6c) so that the reduced pressure trapped between edge 174 and valve AK draws the sample 172 further along the manifold section 150C towards valve AK. Valve BH is then closed and valve AK opened to again apply reduced pressure to the sample leading edge 174 while the sample is restrained by closed valve BH. The sequence of valve operations indicated in FIGS. 6a–6d is repeated to supply progressively reduced trapped volumes of reduced pressure to further draw the sample 172 and position (in the self-limiting manner discussed above) the leading edge 174 at valve AK with the seventy microliter volume extending throughout the length of manifold 150 adjacent the three metering chambers 22, 24 and 26 (28) and the trailing edge 176 in channel section 120 as indicated in FIG. 6e. The rapid sequencing of the valves by controller 21 discussed above positions a metered seventy microliter volume of sample 172 accurately in distribution manifold 150 in a few seconds.

After the sample 172 is positioned in the distribution channel 150 as indicated in FIG. 6c, the sample chambers 22, 24, 26 (or 28) are sequentially filled and the reagent metering chambers 30, 32 and 34 are concurrently filled from their respective reagent reservoirs 50, 54 and 66.

A diagram of the glucose metering network is shown in FIG. 2, the urea and creatinine metering networks being similar. Glucose sample metering chamber 22 is connected between isolation valves 20BB and 20CB while glucose reagent measuring chamber 30 is connected between isolation valves 20AF and 20DD. Connected between isolation valve 20DD and metering chamber 30 is vent valve 20DC. A bypass channel 128G parallels sample chamber 22 and extends from isolation valve 20BA to isolation valve 20DB. Three T valves 20BA, 20BB and 20BC are connected to the glucose section 150G of distribution manifold 150. T valve 20CB connects the outlet 126G of sample metering chamber 22 to bypass channel 128G. A channel 130G extends from isolation valve 20DB to isolation valve 20EB—channel 130G being connectable via T valve 20DA to vacuum manifold 36 and via T valve 20EA to flush preheater 76 (which preheater may be omitted if it is not necessary to thermally equilibrate the flush prior to introduction into the flow network). Vacuum manifold 38 is connected by channel 148G to isolation valve 20DD, T valve 20ED connects channel 148G via channel 146G to the outlet of analysis cell 10 and valve 20EC vents channel 146G.

The pump includes chamber 40 (similar to but of larger volume than valves 20), T valve 20AB and isolation valve 20AE, chamber 40 and valves 20AB and 20AE being operated in sequence as a positive displacement device that flows flush liquid through sample inlet line 120 and probe 16 for cleaning.

The greater negative pressure provided by vacuum manifold 38 is used for degassing and relatively rapid movements of liquid while the regulated lesser negative pressure provided by vacuum manifold 36 provides force appropriate to move the liquids at reasonable speed without drawing gasses through or from them (debubbling). Photometer cell 10 has an inlet port 80 at its bottom and an outlet port 84 at its top that is connected to vacuum manifold 38 through isolation valve 20ED. As the volume of the reagent-sample mixture is less than that of photometer chamber 10, the reduced pressure used to draw the reagent sample mixture into the chamber without filling it also draws following air through the mixture for further mixing and then degassing. After analysis, the sample-reagent mixture is withdrawn through the inlet port 80 and isolation valves 20EB and 20DA to the vacuum manifold 36, the top port 84 of the analysis cell 10 being vented by vent valve 20EC during this sequence.

Further details of the metering, dilution, analysis and flushing sequences may be seen with reference to FIG. 7. FIG. 7a shows the sample 172 to be analyzed (symbolized by dark lines) held in distribution manifold 150 with its leading edge 174 blocked (at valve AK) and its trailing edge 176 exposed to atmosphere through open valve AC and sample probe 16. Valves DA, DB and CB are opened to apply negative pressure (symbolized by dots) from manifold 36 to reduce the pressure in sample metering chamber 22 and bypass channel 128G; and valve DD is opened to similarly reduce the pressure in reagent metering chamber 30. Valve CB is then closed and valve BB is opened so that the reduced pressure trapped in sample metering chamber 22 draws sample 172 into that chamber towards closed valve CB as indicated in FIG. 7b. Concurrently, isolation valve DD is closed, and then valve AF is opened so that the reduced pressure trapped in reagent metering chamber 30 draws reagent 178 (symbolized by slant lines) from reservoir 50 through valve AF into chamber 30.

Figure 7A:
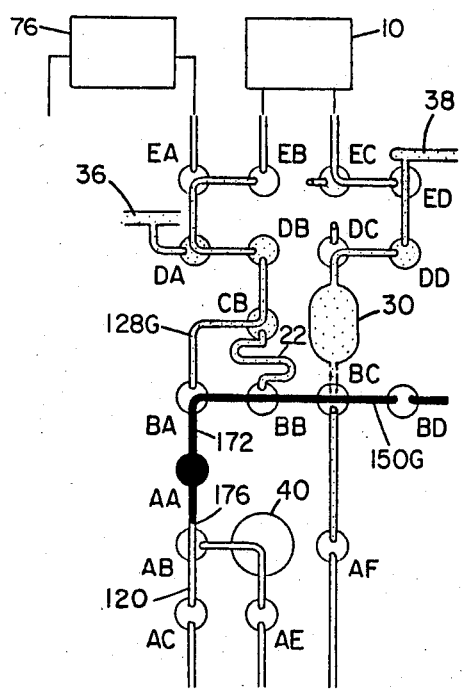
FIG. 7 is a series of diagrams showing an operational sequence of the apparatus shown in FIG. 1.
Figure 7B:
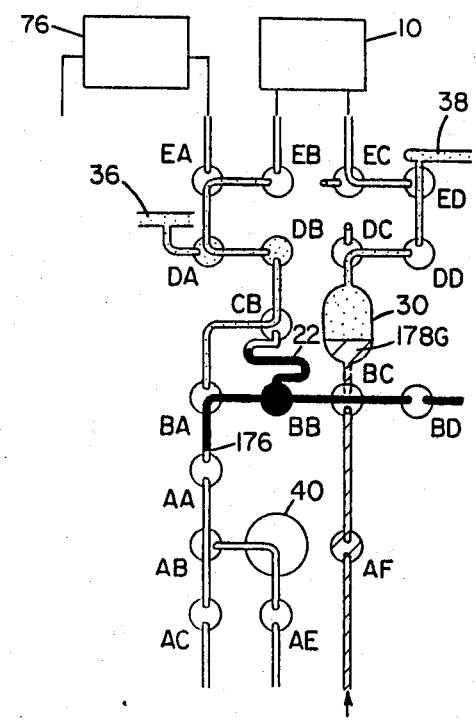
Figure 7C:
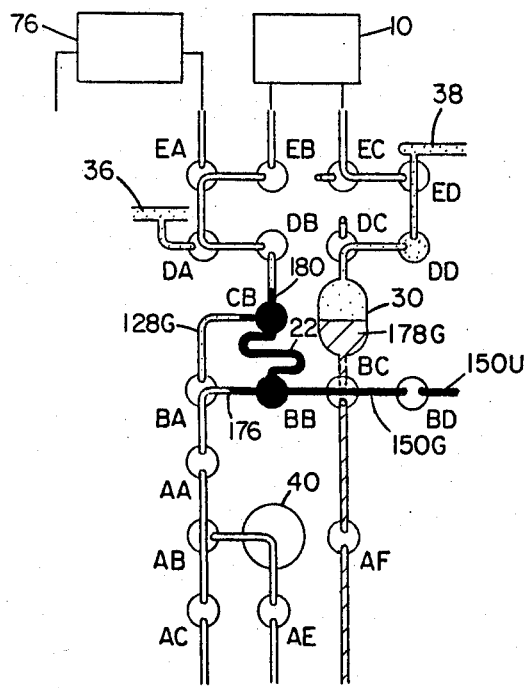
Figure 7D:
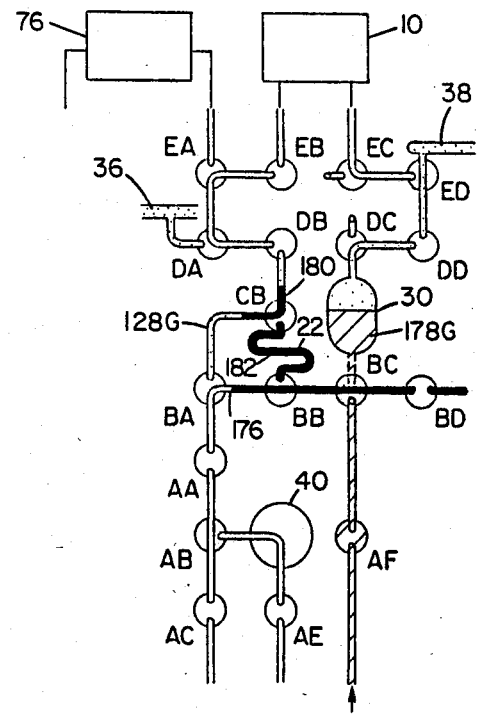

Valves DA and DB are then closed and valve CB opened so that the leading portion 180 of sample is drawn through metering chamber 22 into portions of the bypass channel 128G as indicated in FIG. 7c. Valves BB and CB are then closed, isolating the metered quantity 182 of sample 172 in chamber 22, as indicated in FIG. 7d, from leading portion 180 as well as from trailing portion 176.

The other two sample metering chambers 24, 26 (28) are then similarly filled in sequence. During the sequential filling of the three sample metering chambers, the reagent metering chambers 30, 32 and 34 are concurrently filled by alternately closing and opening valves DD and AF (and corresponding valves DH and AG and DL and AJ) to draw reagents 178G, U and C into the metering chambers 30, 32 and 34 respectively (valve DD being opened to recharge metering chamber 30 with reduced pressure while the reagent 178G is clamped by closed valve AF as indicated in FIG. 7c; then valve DD is closed to trap the reduced pressure in metering chamber 30 and line 144; and then valve AF is opened (as indicated in FIG. 7d) to allow the trapped reduced pressure to draw reagent 178G further into metering chamber 30). The alternate opening and closing of valves DD and AF (and corresponding valves) in each of the three reagent metering chamber flow paths fills the respective metering chambers up to but not beyond valves DD, DH and DL in self-limiting manner similar to the filling of manifold 150 described above in connection with FIGS. 5 and 6.

Figure 7E:
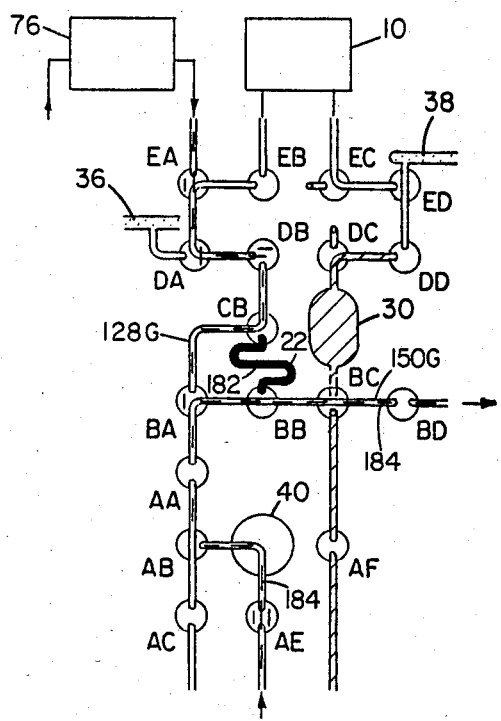

After the three sample metering chambers 22, 24, 26 (28) have been filled, valve AK is opened to draw the excess sample 172 from the distribution manifold 150, and then valves AE and AB are opened to draw flush solution 184 (symbolized by dashed lines) from reservoir 46 through distribution manifold 150 in flushing and cleaning action. Valves AA and AB are then closed and valves EA, DB and BA are opened to draw flush 184 through preheater 76 and then flow through valves EA, DA, DB, CB and BA into the distribution manifold 150 for flushing out the leading portions 180 of sample 172 that have been held in the bypass channel 128G (FIG. 7e). The urea and creatinine channels are similarly flushed.

Valve AH is also opened to connect the vacuum tap 58 (FIG. 1) of probe 16 to vacuum chamber 62 and chamber 40 and valves AB and AE of the pump array are operated in sequence to provide positive displacement pump action to draw flush solution 184 from reservoir 46 and to flow it in the reverse direction through probe 16 where the discharged flush solution 184 is drawn from probe tip 148 by tap 58 through valve AH to vacuum chamber 62. In pump operation, valve AE is opened and then the volume of pump chamber 40 is increased to draw flush solution into that chamber. Valve AE is then closed, valve AB opened and the pump chamber 40 is collapsed (membrane 154 is seated against face plate 152) to force the volume of liquid from chamber 40 out through valve AC and sample probe 16.

After the pumping operation is stopped, valve AA is opened to vent the distribution manifold 150 and remove the flush solution. Reagent vent valve DC and isolation valve DD are opened and the excess reagent 178 in channel 144G is drawn into vacuum manifold 38 and then isolation valve DA is opened to draw flush solution 184 from the bypass channel 128G into manifold 36. Valves BA, DB and DA are pulsed to provide a pulsating liquid flow and enhanced cleaning action. Valves BA, DA and DB are then closed and valves AA, BH and BD are similarly pulsed to clean and air dry the distribution manifold 150. Those valves are then closed, isolating segments 150G, 150U and 150C of the distribution manifold associated with each analysis channel.

After the channels have been cleaned and isolated, vent valve DC and isolation valve BC are opened, connecting reagent measuring metering chamber 30 to the isolated segment 150G of distribution manifold 150; valve BA is opened, connecting that isolated segment 150G to bypass channel 128; and T valve ED is opened to apply reduced pressure from vacuum manifold 38 to analysis cell 10 for about ¼ second. Valve ED is then closed, trapping the reduced pressure in cell 10 and in those portions of flow network 18 connected to cell inlet 80.

Figure 7F:
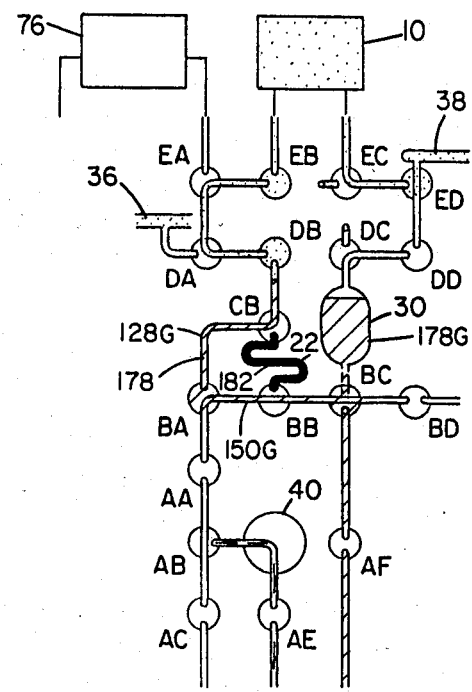
Figure 7G:
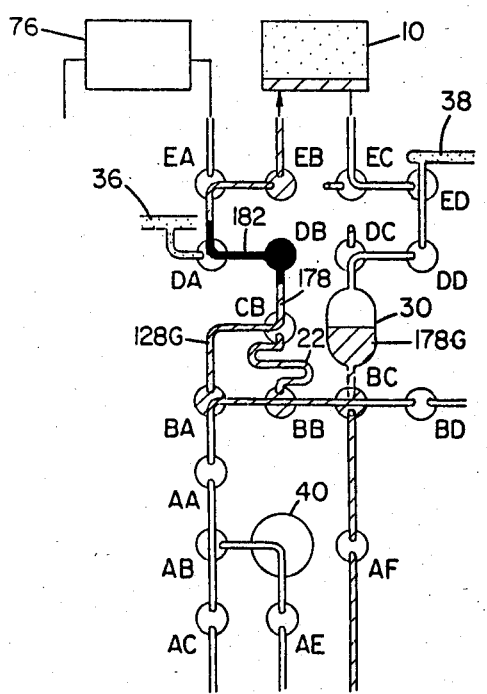
Figure 7H:
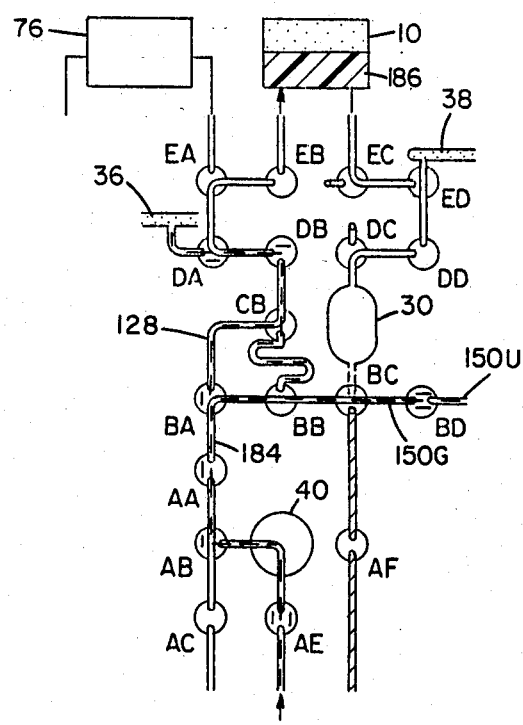

With reference to FIG. 7f, the opening of valves EB and DB applies that reduced pressure to the bypass channel 128G and the isolated segment 150G of distribution manifold 150 to draw reagent 178G from chamber 30 (vented by open vent valve DC) through open valve BC, distribution channel segment 150G and bypass channel 128G towards analysis cell 10. After an interval of about ½ second, valve EB is closed and valve ED is opened to recharge the reduced pressure in the analysis cell. During this interval, the sample chamber isolation valves BB and CB are also opened. After analysis chamber 10 has been recharged with reduced pressure, isolation valve ED is again closed and isolation valve EB is opened so that the metered sample quantity 182 is drawn from chamber 22 followed by a flow of reagent 178 through sample chamber 22 (valve BA being closed during this interval). After the metered sample 182 has been entirely flowed from metering chamber 22, as indicated in FIG. 7g, isolation valve CB is closed and valve BA is opened so that flow of reagent continues through the bypass channel 128G until the entire metered quantity of reagent 178 (together with the metered sample quantity 182) has been flowed into analysis cell 10, the reagent flow alternating between sample chamber 22 and bypass channel 128. During this flow, valves EB and ED are alternately opened and closed to recharge the reduced pressure head in analysis chamber 10. Following air is bubbled through the mixture 186 (symbolized by alternating heavy and light slant lines) in analysis cell 10 from the open vent valve DC to provide further mixing and then vent valve DC is closed for debubbling of the diluted sample mixture 186 in analysis cell 10. Isolation valve EB is then closed (FIG. 7h) preparatory to photometric analysis.

Vent valve EC is opened during photometric analysis to vent analysis cell 10. During that interval, distribution manifold valves (AA, BD, BH and AK) are opened as are valves AE and AB to draw flush solution 184 through the distribution manifold 150; then valves BB, CB, DB and DA are opened to draw flush solution 184 through sample metering chamber 22 to vacuum manifold 36; then valve BA is opened to flow flush solution 184 through the bypass channel 128; then flush solution flow is then turned off and valve AC is opened to vent the lines to atmosphere, valves BB, CB, BA, DB being pulsed as air is flowed through them to clean and dry the lines in preparation for the next analysis sequence.

After the spectrophotometric analysis, valves EB and DA are opened to apply reduced pressure to the input 80 of analysis chamber 10 to draw the analyzed mixture 186 from that chamber for discharge through manifold 36 into vacuum chamber 62. Vent valve EC and isolation valve DA are then closed and valves EA and ED are opened to draw flush solution 184 through analysis chamber 10 and vacuum manifold 38 for discharge into vacuum chamber 62 in a cleaning of the analysis chamber. The analysis chamber is then vented and the valves EB and DA are pulsed and then turned off so that the channel is in condition for the next analysis cycle.

Similar mixing and photometric analyses of the metered quantities of sample and reagents in the urea and creatinine channels and then flushing and cleaning of those channels in preparation for the next analysis sequence proceeds concurrently.

While a particular embodiment of the invention has been shown and described, various modifications will be apparent to those skilled in the art, and therefore it is not intended that the invention be limited to the disclosed embodiment or to details thereof and departures may be made therefrom within the spirit and scope of the invention.

What is claimed is:

1. A liquid handling system comprising, inlet port structure for introduction of a liquid sample, auxiliary liquid storage structure, reduced pressure reservoir structure, flow network structure connected to said inlet port structure, said flow network structure including sample metering chamber structure and auxiliary liquid metering chamber structure, each said metering chamber structure having an inlet and an outlet, means for applying reduced pressure from said reservoir structure to the outlet of said sample metering chamber structure to fill said sample metering chamber by drawing sample liquid to be analyzed through said inlet port structure into said sample metering chamber structure, means for applying reduced pressure from said reservoir structure to the outlet of said auxiliary liquid metering chamber to fill said auxiliary liquid metering chamber by drawing auxiliary liquid from said auxiliary liquid storage structure into said auxiliary liquid metering chamber structure, and flow control means including means for flowing the metered quantities of said sample liquid and said auxiliary liquid to form a mixture of said sample and auxiliary liquids.

2. The system of claim 1, and further including analysis chamber structure, said analysis chamber structure having an inlet at the bottom of the chamber and an outlet at the top of the chamber, and said flow control means is arranged to flow said metered quantities of said sample liquid and said auxiliary liquid into said analysis chamber through said inlet for analysis and to remove the mixture of said metered quantities from said analysis chamber through said inlet after analysis.

3. The system of claim 1 and further including valve structure connected between the outlet of said sample metering chamber structure and said reduced pressure reservoir structure for applying a limited volume of reduced pressure to said sample metering chamber so that said sample liquid is not drawn past said valve structure while said sample metering chamber structure is being filled.

4. The system of claim 1 wherein said flow network structure further include a bypass channel that extends between the inlet and outlet of said sample metering chamber, a first valve for controlling communication between said sample metering chamber inlet and said bypass channel, a second valve for controlling communication between said bypass channel and the outlet of said sample metering chamber, and said flow control means includes means for operating said first and second valves to flow auxiliary liquid from said auxiliary metering chamber through said bypass channel during a first interval, and then through said sample metering chamber during a subsequent interval so that flow of auxiliary liquid to said analysis chamber precedes and follows the metered quantity of sample liquid flowed from said sample metering chamber.

5. The system of claim 1 wherein said reduced pressure reservoir structure includes means for providing reduced pressure at two different values.

6. The system of claim 5 wherein said flow control means includes means for applying reduced pressure at one of said values to said auxiliary liquid metering chamber to fill said auxiliary liquid metering chamber, and means for concurrently applying reduced pressure at a second value to said outlet of said sample metering chamber structure to fill said sample metering chamber.

7. The system of claim 1 wherein the volume of said auxiliary liquid metering chamber structure is at least ten times the volume of said sample metering chamber structure.

8. The system of claim 1 wherein there are a plurality of analysis chamber structures, and said flow network structure includes a plurality of sample metering chambers and auxiliary liquid metering chambers corresponding to said plurality of analysis chamber structures, and a distribution manifold connected to said inlet port structure for supplying sample liquid to be analyzed to said plurality of sample metering chambers.

9. The system of claim 8 wherein the volume of said distribution manifold is less than 0.5 milliliter.

10. The system of claim 8 wherein said flow control means connects said plurality of sample metering chambers to said distribution manifold sequentially, and concurrently connects said plurality of auxiliary liquid metering chambers to corresponding auxiliary liquid storage reservoirs so that said auxiliary liquid metering chambers are filled concurrently while said sample metering chambers are being filled sequentially.

11. The system of claim 8 wherein said distribution manifold is in said flow network structure and a series of valves are disposed along said distribution manifold between said inlet port structure and said reduced pressure reservoir structure, and said flow control means operates said distribution manifold valves to isolate segments of the sample in said distribution manifold while said sample metering chambers are being filled, the volume of each said isolated sample segment being less than fifty microliters.

12. The system of claim 1 wherein said flow network structure is an array that includes
a face plate member that has a rigid surface,
a flexible valve sheet member that has a surface that is softer and more resilient than said face plate surface for mating engagement with said face plate surface,
a network of channel portions in one of said members with a plurality of valve land portions, each said valve land portion being located between two adjacent ones of said channel portions, the surfaces of said land portions being coincident with the surface of the member in which they are located,
and a valve control arrangement that includes a plurality of valve actuators, each said actuator being arranged to flex said sheet member between a first position in which said valve sheet surface is in mating and sealing engagement with said valve face plate surface to sealingly block flow between adjacent ones of said channel portions, and a second position in which said sheet surface is spaced away from said first position to allow flow between said adjacent channel portions across the land portion corresponding to that actuator.

13. The system of claim 12 wherein said auxiliary liquid metering chamber is formed in said face plate member, and said sample metering chamber is in the form of a groove that extends along the surface of said face plate member.

14. The system of claim 12 wherein each said valve has a volume of less than ten microliters when open and essentially zero dead space when closed.

15. The system of claim 12 and further including positive displacement pump structure including two pump valves, a pump chamber defined between said face plate and said sheet member, and pump chamber actuator structure arranged to flex said sheet member between a first position in which said valve sheet is in mating and sealing engagement with said rigid face plate surface and a second position in which said sheet surface is spaced away from said first position to define a pump chamber of volume that is at least twice the volume of either of said pump valves in its open position.

16. The system of claim 1 wherein said sample metering chamber structure has a volume of less than 0.1 microliters and the volume of said auxiliary liquid metering chamber structure is at least ten times the volume of said sample metering chamber structure.

17. The system of claim 1 wherein there are a plurality of analysis chamber structures, and said flow network structure includes a plurality of sample metering chambers and auxiliary liquid metering chambers corresponding to said plurality of analysis chamber structures, a distribution manifold in said flow network structure and connected to said inlet port structure for supplying sample liquid to be analyzed to said plurality of sample metering chambers, and a series of valves disposed along said distribution manifold between said inlet port structure and said reduced pressure reservoir structure for isolating segments of the sample in said distribution manifold while said sample metering chambers are being filled, the volume of said distribution manifold being less than 0.5 milliliter, the volume of each said isolated sample segment being less than fifty microliters, and each said valve having a volume of less than ten microliters when open and essentially zero dead spaced when closed.

18. A liquid handling system comprising analysis chamber structure having an inlet and an outlet,
inlet port structure for introduction of a liquid sample to be analyzed,
auxiliary liquid storage structure,
reduced pressure reservoir structure,
flow network structure connected between said sample inlet and said analysis chamber structure,
said flow network structure including sample metering chamber structure that has an inlet and an outlet, a bypass channel that extends between the inlet and outlet of said sample metering chamber, a first valve for controlling communication between said sample metering chamber inlet and said bypass channel, a second valve for controlling communication between said bypass channel and the outlet of said sample metering chamber, means for applying reduced pressure from said reservoir structure to the outlet of said sample metering chamber structure to fill said sample metering chamber by drawing sample liquid to be analyzed through said inlet port structure into said sample metering chamber structure, and flow control means including means for operating said first and second valves to flow auxiliary liquid through said bypass channel during a first interval, and then through said sample metering chamber during a subsequent interval so that flow of auxiliary liquid to said analysis chamber precedes and follows the metered quantity of sample liquid flowed from said sample metering chamber to said analysis chamber.

19. The system of claim 18 and further including auxiliary liquid metering chamber structure that has an inlet and an outlet, and means for applying reduced pressure from said reservoir structure to the outlet of said auxiliary liquid metering chamber to fill said auxiliary liquid metering chamber by drawing auxiliary liquid from said storage structure into said auxiliary liquid metering chamber while said sample metering chamber structure is being filled.

20. The system of claim 19 and further including valve structure connected between the outlet of said sample metering chamber structure and said reduced pressure reservoir structure for applying a limited volume of reduced pressure to said sample metering chamber so that said sample liquid is not drawn past said valve structure while said sample metering chamber structure is being filled.

21. The system of claim 20 and further including flush liquid storage structure, means for applying reduced pressure from said reservoir structure to ports of said flow network structure for flowing flush liquid through said flow network structure for cleaning said flow network between analysis sequences.

22. The system of claim 18 wherein said flow network structure is an array that includes a face plate member that has a rigid surface, a flexible valve sheet member that has a surface that is softer and more resilient than said face plate surface for mating engagement with said face plate surface, a network of channel portions in one of said members with a plurality of valve land portions, each said valve land portion being located between two adjacent ones of said channel portions, the surfaces of said land portions being coincident with the surface of the member in which they are located, and a valve control arrangement that includes a plurality of valve actuators, each said actuator being arranged to flex said sheet member between a first position in which said valve sheet surface is in mating and sealing engagement with said valve face plate surface to sealingly block flow between adjacent ones of said channel portions, and a second position in which said sheet surface is spaced away from said first position to allow flow between said adjacent channel portions across the land portion corresponding to that actuator.

23. The system of claim 22 wherein each said valve has a volume of less than ten microliters when open and essentially zero dead spaced when closed.

24. The system of claim 23 and further including positive displacement pump structure including two pump valves, a pump chamber defined between said face plate and said sheet member, and pump chamber actuator structure arranged to flex said sheet member between a first position in which said valve sheet is in mating and sealing engagement with said rigid face plate surface and a second position in which said sheet surface is spaced away from said first position to define a pump chamber of volume that is at least twice the volume of either of said pump valves in its open position.

25. An analysis system comprising a plurality of analysis chamber structures, each said analysis chamber structure having an inlet and an outlet, inlet port structure for introduction of a liquid sample to be analyzed, a plurality of liquid reagent storage structures, reduced pressure reservoir structure, flow network structure connected between said sample inlet and said analysis chamber structure, said flow network structure including a plurality of sample metering chamber structures and a corresponding plurality of reagent liquid metering chamber structures, each said metering chamber structure having an inlet and an outlet, and a distribution manifold connected between said inlet port structure and the inlets of said sample metering chambers for supplying sample liquid to be analyzed to said plurality of sample metering chambers, means for applying reduced pressure from said reservoir structure to said distribution manifold sample metering chamber structure to draw sample liquid to be analyzed through said inlet port structure into said distribution manifold, means for applying reduced pressure from said reservoir structure sequentially to the outlets of said sample metering chamber structures to fill said sample metering chamber by drawing sample liquid from said distribution manifold into said sample metering chamber structures, means for applying reduced pressure from said reservoir structure to the outlets of said reagent liquid metering chambers to fill said reagent liquid metering chambers by drawing reagent liquid from said reagent liquid storage structure into said reagent liquid metering chamber structures while said sample metering chambers are being filled from said distribution manifold, and flow control means including means for connecting the inlet of each said reagent liquid metering chamber structure to the inlet of the corresponding sample metering chamber structure and the outlet of each said sample metering chamber structure to the inlet of the corresponding analysis chamber structure, and means for applying reduced pressure to the outlets of said analysis chamber structures while the inlets of the corresponding sample and reagent liquid metering chambers are connected together to flow the metered quantities of said sample liquid and said reagent liquids from said sample metering and reagent liquid metering chambers to said analysis chambers.

26. The system of claim 25 wherein said flow network structure is an array that includes a face plate member that has a rigid surface, a flexible valve sheet member that has a surface that is softer and more resilient than said face plate surface for mating engagement with said face plate surface, a network of channel portions in one of said members with a plurality of valve land portions, each said valve land portion being located between two adjacent ones of said channel portions, the surfaces of said land portions being coincident with the surface of the member in which they are located, and a valve control arrangement that includes a plurality of valve actuators, each said actuator being arranged to flex said sheet member between a first position in which said valve sheet surface is in mating and sealing engagement with said valve face plate surface to sealingly block flow between adjacent ones of said channel portions, and a second position in which said sheet surface is spaced away from said first position to allow flow between said adjacent channel portions across the land portion corresponding to that actuator.

27. The system of claim 26 wherein each said sample metering chamber structure has a volume of less than 0.1 microliter and the volume of said reagent liquid metering chamber structure is at least ten times the volume of said sample metering chamber structure, a series of valves are disposed along said distribution manifold between said inlet port structure and said reduced pressure reservoir structure for isolating segments of the sample in said distribution manifold while said sample metering chambers are being filled, the volume of said distribution manifold being less than 0.5 milliliter, the volume of each said isolated sample segment being less than fifty microliters, and each said valve having a volume of less than ten microliters when open and essentially zero dead spaced when closed, and said flow control means connects said plurality of sample metering chambers to said distribution manifold sequentially, and concurrently connects said plurality of reagent liquid metering chambers to corresponding reagent liquid storage reservoirs so that said reagent liquid metering chambers are filled concurrently while said sample metering chambers are being filled sequentially.

28. The system of claim 27 wherein said flow network structure further include a bypass channel that extends between the inlet and outlet of said sample metering chamber, a first valve for controlling communication between said sample metering chamber inlet and said bypass channel, a second valve for controlling communication between said bypass channel and the outlet of said sample metering chamber, and said flow control means includes means for operating said first and second valves to flow reagent liquid from said reagent liquid metering chamber through said bypass channel during a first interval, and then through said sample metering chamber during a subsequent interval so that flow of reagent liquid to said analysis chamber precedes and follows the metered quantity of sample liquid flowed from said sample metering chamber.

29. The system of claim 28 wherein said reduced pressure reservoir structure includes means for providing reduced pressure at two different values, and said flow control means includes means for applying reduced pressure at one of said values to said reagent liquid metering chambers to fill said reagent liquid metering chambers, and means for concurrently applying reduced pressure at a second value to said outlet of said sample metering chamber structures to fill said sample metering chambers.

30. The system of claim 28 wherein each said analysis chamber structure has an inlet at the bottom of the chamber and an outlet at the top of the chamber, and said flow control means is arranged to flow said metered quantities of said sample liquid and said reagent liquid from corresponding sample and reagent metering chambers into said analysis chambers through said inlets for analysis and to remove said metered quantities from said analysis chambers through said inlets after analysis.

31. The system of claim 25 wherein a series of valves are in said distribution manifold between said inlet port structure and said reduced pressure reservoir structure to isolate portions of said distribution manifold and corresponding sample metering chambers.

32. The system of claim 25 and further including flush liquid storage structure, means for applying reduced pressure from said reservoir structure to said flow network structure to draw flush liquid through said flow network structure, and said flow control means includes means for connecting said flush liquid storage structure to said flow network structure to flush excess sample from said distribution manifold after said sample metering chambers are filled, and to connect said flow network structure to said flush liquid storage structure during the analysis sequence to clean said flow network structure during said analysis of the sample mixtures in said analysis chambers.

33. A system for precise dilution of a liquid comprising:

a face plate member that has a substantially rigid surface, a flexible sheet member that has a surface at least part of which is adapted for mating engagement with corresponding parts of the rigid face plate surface, a network of channels in at least one of the members, first and second chamber regions in said face plate member for isolating accurately predetermined volumes of liquid and for passing said accurately predetermined volumes of liquid to a channel of the network to form a diluted mixture, a plurality of valve lands in said one member, each of which separates at least two adjacent channels in a member, the lands having surfaces adapted for releasably mating with corresponding parts of the surface of the other member, a plurality of valve actuators, each associated with a valve land and adapted to flex the sheet member between a first position, in which the valve land of one member mates with the corresponding part of the surface of the other member, and a second position, in which the sheet member is spaced away from the first position to allow flow across the land and between the adjacent channels, and means for flowing liquid through the system.

34. The system of claim 33 wherein said face plate member is transparent and said sheet member is opaque.

35. The system of claim 33 wherein one of said chamber regions is a reagent liquid metering chamber formed in said face plate member, and the other of said chamber regions is a said sample metering chamber in the form of a groove that extends along the surface of said face plate member.

36. The system of claim 35 wherein said sample metering chamber has a volume of less than 0.1 microliter and the volume of said reagent liquid metering chamber is at least ten times the volume of said sample metering chamber structure, and each said valve has a volume of less than ten microliters when open and essentially zero dead spaced when closed.

* * * * *